(12) United States Patent
Lynnworth et al.

(10) Patent No.: US 6,349,599 B1
(45) Date of Patent: Feb. 26, 2002

(54) LAYERED ULTRASONIC COUPLER

(75) Inventors: Lawrence C. Lynnworth, Waltham; Yi Liu, Bolton, both of MA (US)

(73) Assignee: Panametrics, Inc., Waltham, MA (US)

( * ) Notice: Subject to any disclaimer, the term of this patent is extended or adjusted under 35 U.S.C. 154(b) by 0 days.

(21) Appl. No.: 09/563,474

(22) Filed: May 2, 2000

(51) Int. Cl.[7] ............................................. G01N 29/00
(52) U.S. Cl. ........................................................ 73/644
(58) Field of Search ................... 73/644, 617; 600/459, 600/443, 444, 445, 446, 447

(56) References Cited

U.S. PATENT DOCUMENTS

| | | | | |
|---|---|---|---|---|
| 3,663,842 A | * | 5/1972 | Miller | 73/644 |
| 4,019,373 A | * | 4/1977 | Freeman et al. | 73/644 |
| 4,454,767 A | * | 6/1984 | Shinkai et al. | 73/861.18 |
| 4,556,066 A | * | 12/1985 | Semrow | 128/660 |
| 4,961,347 A | * | 10/1990 | Arakawa et al. | 73/644 |
| 5,029,474 A | * | 7/1991 | Schulze | 73/587 |
| 5,078,149 A | * | 1/1992 | Katsumata et al. | 128/662.03 |
| 5,522,878 A | * | 6/1996 | Montecalvo et al. | 607/152 |

* cited by examiner

Primary Examiner—Hezron Williams
Assistant Examiner—Rose M. Miller
(74) Attorney, Agent, or Firm—Nutter, McClennen & Fish LLP

(57) ABSTRACT

An ultrasonic coupling assembly includes a barrier layer that contacts the wall, and a generally thicker layer formed of a compliant material such as zinc foil that extends over the first layer. A third layer may cover and enclose the compliant layer, e.g., by folding the first layer over and on top of the second layer to cover the edge faces thereof. An exemplary embodiment is implemented using gold foil approximately one mil thick for the first layer, and zinc sheeting approximately four mils thick for the second layer. Use of inert top and bottom, or outside, layers prevents the inadvertent installation of the coupling element with the compliant layer directly contacting the wall. Disk embodiments may employ a stack of separate disks formed of foils or sheets of the respective materials. For cryogenic applications, a material such as indium may be used for the second layer without risk of its alloying or migration through the first layer.

18 Claims, 3 Drawing Sheets

LAYERED ULTRASONIC COUPLER

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to ultrasonic transducers and to methods and articles for coupling ultrasonic transducers to structures such as the wall of a conduit or tank so that the transducer effectively transmits an ultrasonic signal into and generally through the wall to perform various kinds of measurement or interrogation of a fluid contained by the conduit or tank. This field of industrial instrumentation is highly developed, and various forms of transducers as well as a number of different structures for coupling those transducers to a solid wall have been developed. One typical ultrasonic interrogation procedure is to transmit a short ultrasonic pulse bidirectionally across a fluid along a diagonal path having some component in the direction of fluid flow, and to detect changes in transit time indicative of flow velocity. Other procedures may employ continuous waves, or may process scattered energy to detect a frequency change or other parameter of interest. Often, a physical parameter such as temperature or fluid density may be determined by processing the received signals.

The measurement apparatus may involve permanently mounted transducers that thread into tapped openings in the wall, or into specially machined receiving sockets that, in turn, thread into the wall or are welded thereto. Often, however, for reasons of economy, convenience or even necessity, the ultrasonic transducer or signal assemblies are simply clamped in a desired position against the wall to perform a measurement. In that case, care must be taken to assure that there is effective ultrasonic coupling between the transducer and the conduit wall, so that an undistorted signal of sufficient strength is effectively coupled into the wall, and typically through the wall and into the adjacent fluid when the flow or other characteristics of the adjacent fluid are to be measured.

For such clamp-on arrangements, often a strap, chain or U-bolt is used to hold the transducer assembly, or to hold a mounting block that secures the transducer, firmly down against the pipe wall. For certain high temperature applications, the transducer mounts on a standoff or buffer rod assembly, and the proximal face of this buffer must then be secured in effective acoustic contact against the wall. In such a case, typically the transducer is fabricated in, or threaded into, a fitting at one end of the buffer rod opposed to the other end which is to be clamped in contact with the wall. With such clamp-on arrangements, if the wall has an irregular, rough or curved surface, some additional machining preparation, or some further means of enhancing or effecting acoustic coupling must be provided to assure effective coupling.

Many materials have been proposed for achieving such coupling, both in the area of nondestructive testing (where a transducer is typically urged by hand against the wall or metal surface), and in the field of ultrasonic fluid interrogation where clamping elements are often required to fix the transducer at a precisely specified location, often for an extended time.

Among the coupling agents proposed in the past may be found molten glass film, neoprene sheet, Teflon tape, silver-platinum pastes, a gold, platinum, aluminum or zinc foil, and other materials. An extensive listing of known approaches to the coupling of ultrasonic signals appears in the book Ultrasonic Measurements for Process Control by Lawrence C. Lynnworth, Academic Press, (1989) pp. 156–157.

Often before applying one of the listed couplings, the pipe is prepared in some way, for example, by smoothing its surface to minimize the deviations between the wall surface and the buffer or transducer face with which it is to couple. Thus, sanding with abrasive sanding tape may be useful to flatten any peaks or surface protuberances on the conduit, or reduce the height of asperities that would otherwise impair acoustic contact. Foils have sometimes been used to achieve coupling between opposed iron, steel or stainless steel surfaces, and this is effective if the surface finish is adequately smooth. For some applications, synthetic lubricants, anti-seize greases, or thicker or deformably compliant materials of suitable acoustic impedance may be necessary to achieve coupling in the presence of higher surface roughness. The clamping or screw-down pressures necessary for effective coupling may, in some cases, be quite high, about one thousand to several thousand psi, and when a thicker material is employed to effect coupling, attention must also be paid to its strength and modulus, in order to avoid creep, flow or cracking. This is especially true for applications in higher temperature plant conditions, where clamp-on instrumentation is often required.

Often, clamp-on application is required for instrumentation installed after the original plant was laid out, either because awkward conduit positioning, or the inability to shut down or remove a portion of the flow line for machining, prevent non-clamp-on modes of instrument mounting. The clamp-on transducer assembly may then be installed relatively permanently e.g., over ten years, or for extended periods of time such as one to two years between shutdown[s] for maintenance, so that the long term structural or chemical effects of the coupling and clamping assembly must be considered. These long periods may potentially rule out the use of unstable, reactive or unpredictable coupling materials. In application areas such as nuclear power plant engineering, the potential for, or inability to predict, factors such as pressure induced recrystallization, contact alloying, intergranular corrosion by diffusion of a coupling metal whose melting point is too close to the wall temperature, or other fault growth mechanism in the conduit wall that occur as a result of the material of the coupling may be sufficient to preclude use of clamp-on mounting, or to rule out the application of particular coupling structures. For example, zinc, with a melting point of 419° C. may raise problems if clamped to a six millimeter thick conduit of carbon steel or stainless steel carrying fluid of about sixty bar at elevated temperature near 260° C.

Because of these factors, the suitability of a coupling mechanism, either in terms of its ultrasonic coupling performance or its physical effects on the wall with which it is in contact, may be questioned.

Accordingly it is desirable to provide an ultrasonic coupler for dependably mounting a transducer or buffer assembly on a wall or conduit.

It is also desirable to provide an ultrasonic coupling assembly that provides effective coupling, is convenient to install, can be used on a wide variety of conduit wall thicknesses and materials, and resists adverse chemical or physical deterioration.

It is also desirable to provide an ultrasonic coupling assembly compatible with diverse transducers, with different mounting mechanisms, and with a range of conduit or tank wall materials.

SUMMARY OF THE INVENTION

One or more of the above features and other desirable objects are obtained in accordance with the present invention by a coupling assembly having two or more thin metallic layers. A first layer formed of a gold foil or similar inert substance rests against the wall of a conduit or vessel to form a barrier, while a second layer formed of material such as zinc sheet extends over the first layer to effect ultrasonic coupling with the wall through the barrier. In some embodiments, a third layer covers the second layer and may, together with the first layer, form a symmetrical sheath or envelope sandwiching or entirely enclosing the second layer. In one preferred embodiment the third layer is formed of the same material as the first layer, and is provided by folding the first layer over and on top of the second layer thus also covering at least one edge thereof. An exemplary embodiment is implemented using gold foil approximately one mil thick for the first layer and zinc foil approximately four mils thick for the second layer. The use of inert top and bottom, or outside, layers prevents the inadvertent installation of the coupling element with its second layer contacting the wall. The layered structure may be shaped like the contact surface, as a rectangular or disk-shaped pad or stack. Disk embodiments may employ a stack of separate disks formed of foil or sheet of the respective barrier and coupling materials, to be placed over a coupling face. When used for cryogenic applications, the second layer may employ a material such as aluminum or indium (or alloys thereof) without risk of alloying or adverse metallurgical effects such as grain migration through the first layer. In general, the provision of the first foil layer serves as a barrier against migration from the second layer and thus guards against structural failure of the conduit wall due to metallurgical changes when high temperature/high clamping pressure conditions prevail.

BRIEF DESCRIPTION OF THE DRAWINGS

These and other features of the invention will be understood from the description below taken together with illustrations of representative embodiments, wherein.

DETAILED DESCRIPTION

Figure 1:
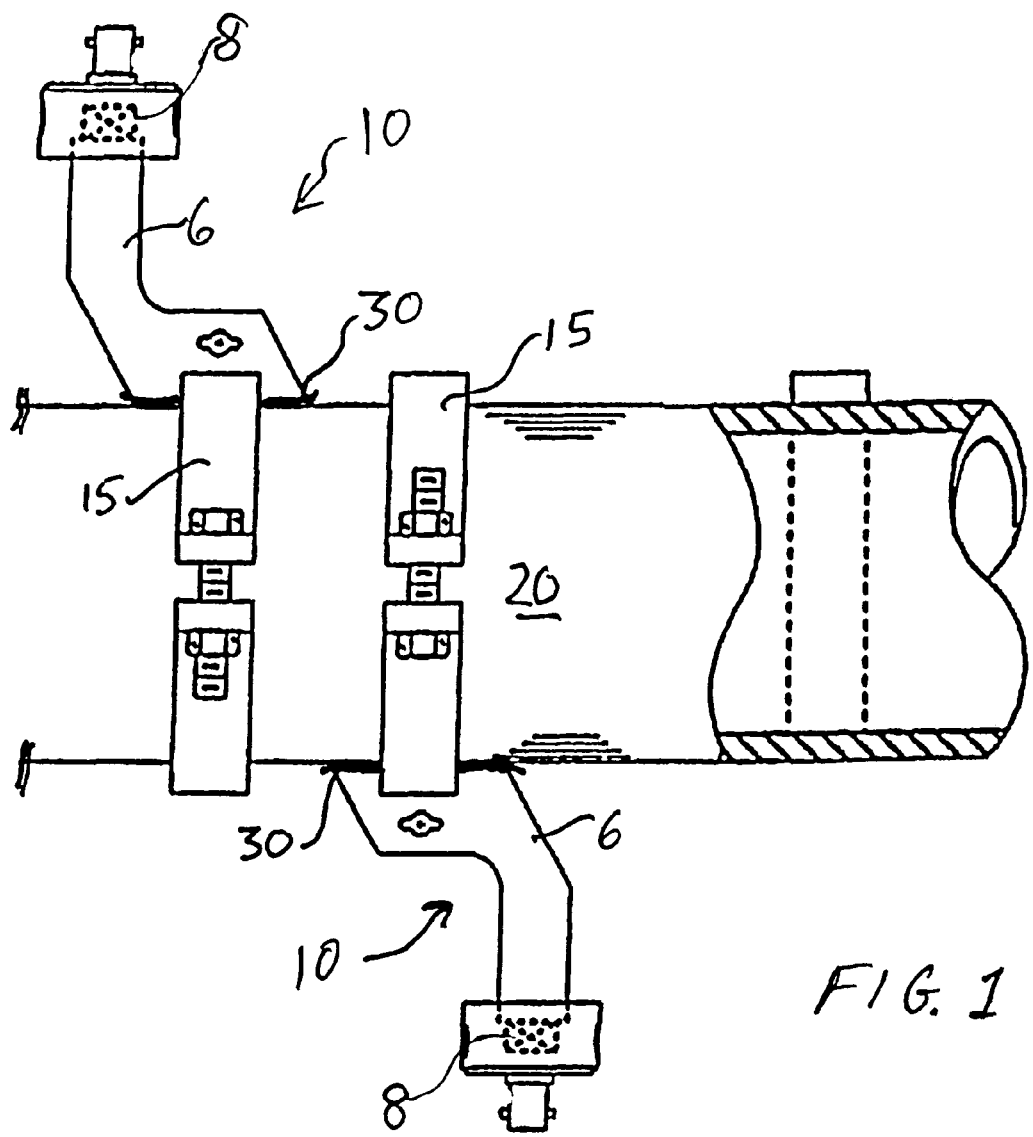
FIG. 1 illustrates a transducer and buffer assembly mounted on a conduit.

FIG. 1 illustrates an ultrasonic signal assembly 10 coupled to the wall of a conduit 20 by a layered ultrasonic coupler 30 in accordance with the present invention which is clamped between the transducer and the wall. For ease of illustration, the ultrasonic signal assembly 10 is illustrated by an assembly colloquially referred to as a "hockey stick" buffered transducer, of the type sold by Panametrics, Inc. of Waltham, Mass. Such assemblies are extensively described in U.S. Pat. No. 6,047,602, wherein a number of embodiments are described having bodies formed as relatively thin plates which propagate an ultrasonic signal pulse at a defined angle for launching from their lower face into the conduit wall. By way of example, the conduit wall may be at an application temperature of 260 to 500° C., or at –200° C. in a cryogenic application. In some embodiments a conventional ultrasonic transducer 8 is fabricated within or screws into a fitting attached to the distal end of the hockey stick, so that the hockey stick constitutes a buffer rod, providing a thermal standoff which protects the transducer element from a hot pipe while providing a signal-preserving waveguide for the pulse launched by the transducer. As illustrated in phantom, the hockey stick 10 is clamped to the conduit 20 by a suitable belt, chain or other clamping mechanism which secures its alignment and provides sufficient pressure (typically, one to several thousand psi) for acoustic contact between the lower face of the hockey stick 6 and the adjacent contact region of the conduit wall.

Figure 2:
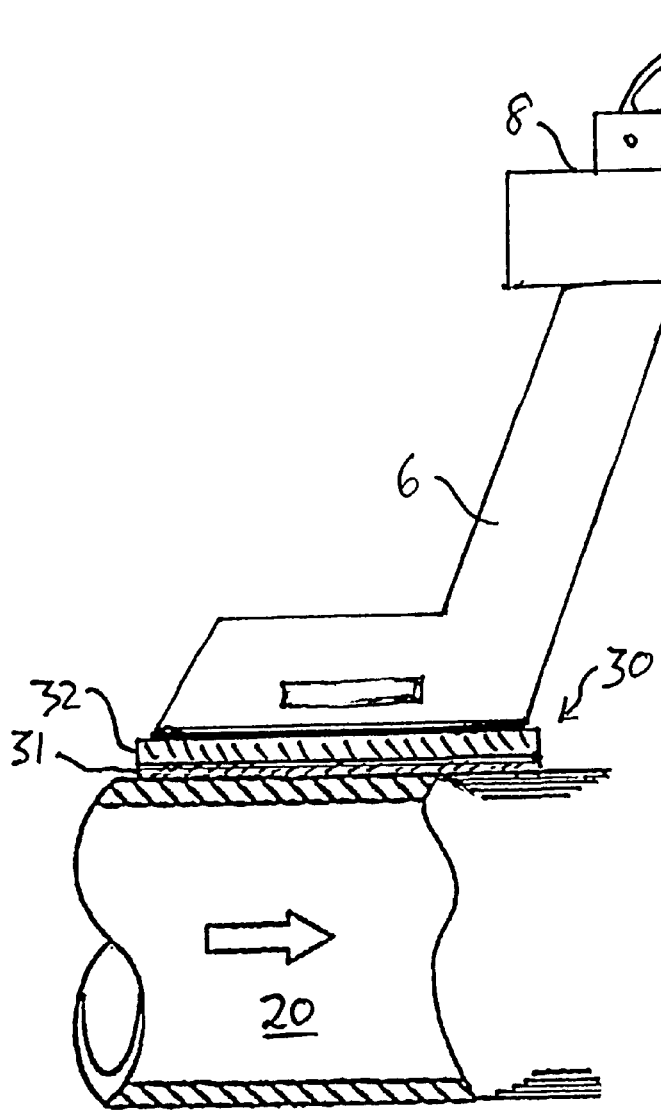
FIGS. 2 and 2A show details of one coupling assembly of the present invention applied to the assembly and conduit of FIG. 1.

The coupling assembly 30 is placed between the hockey stick and the wall to enhance this acoustic coupling. As described more fully below the coupler 30 has a surface compliant structure, and suitable impedance to couple the signal. It will be understood that the couplers described herein may be used with diverse other transducer assemblies or wedge arrangements, and are not limited to the illustrated hockey stick transducer assemblies. As best seen in FIG. 2, the coupler assembly 30 is a layered article or bulk laminate material interposed between the buffer waveguide and the conduit wall. The wall may have a relatively high degree of surface roughness as well as a characteristic curvature of its cylindrical shape, and the lower face of the hockey stick or other ultrasonic transducing assembly, may be milled or otherwise finished so that it is both flat and smooth. The layered coupler includes a barrier layer 31 whose thickness preferably exceeds the height of rough protrusions by a factor of at least two, and most preferably by a factor of about ten. Preferably the conduit wall is smoothed to slightly better than a standard machined finish, i.e., smoother than 125 micro inches rms, and preferably smoother than 50 micro inches.

The layered coupling assembly 30 includes a first layer 31 which directly contacts the conduit wall and functions as a thin barrier layer, and a second or coupling layer 32 of generally thicker gauge. By way of example, layer 31 may comprise a metal foil approximately one mil (25 micrometers) thick, while the second or coupling layer 32 may be substantially thicker. In one embodiment the second layer is formed of sheet zinc approximately four mils (100 micrometers) thick. The zinc has a relatively low modulus, and it readily and intimately conforms both to the roughness and curvature of the conduit when a relatively low clamping pressure is applied. The gold foil serves as a barrier layer to prevent migration of the relatively mobile and potentially reactive zinc into the conduit wall. For temperatures above 350° C. or 400° C., which are close to the melting point of zinc, silver is an alternative. A useful rule of thumb is to make sure the coupling layer material has a melting or eutectic point at least 20° C. above the maximum application temperature.

Figure 2A:
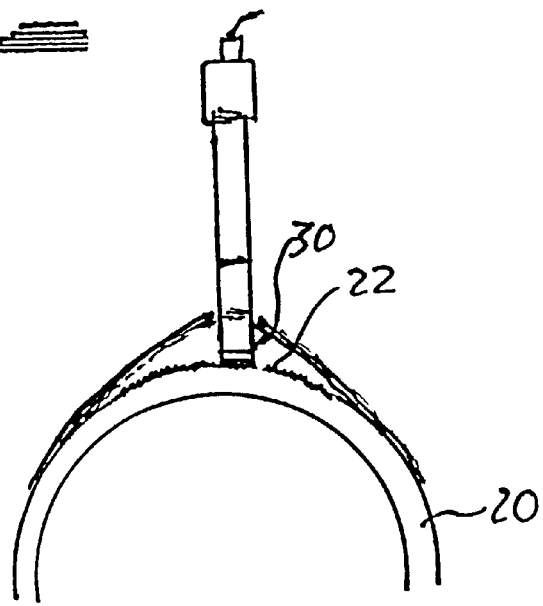
Figure 4:
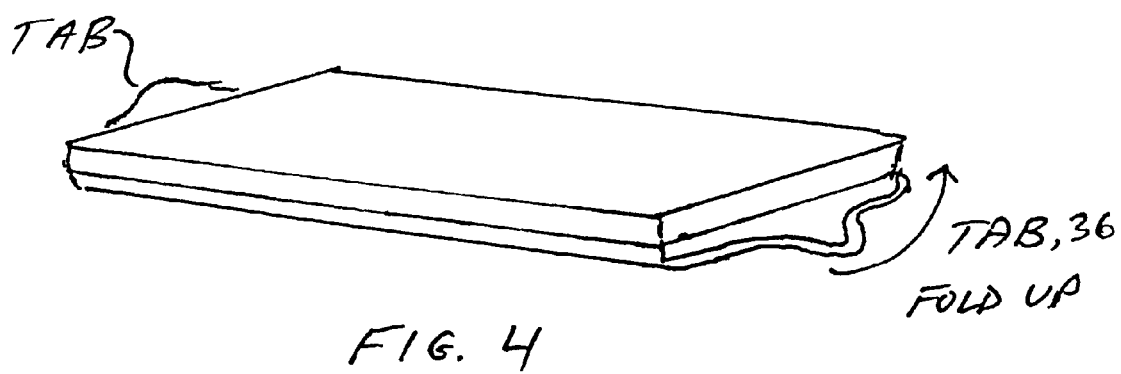
FIG. 4 illustrates a detail of construction useful with various embodiments of the invention.

FIG. 2A illustrates a somewhat enlarged view of the coupling element 30 of FIG. 2. As shown in FIG. 2, the coupling element may consist essentially of the stack of layers of barrier or inert metal, layer 31, and a thicker layer of coupling material, e.g., zinc layer 32. The laminated structure is sized to cover the coupling face of the buffer rod or ultrasonic transducer assembly 10, and may further include an extending end portion 36 in the form of a small tab, as shown in FIG. 4, which allows attachment and facilitates alignment of the coupler to the transducer assembly 10 during the course of fitting and clamping the assembly on a pipe. Such tabs may be provided at opposed ends or sides of the coupler, and the tabs may be bent up against the body of the buffer rod or transducer assembly, and may be secured to the transducer assembly with tape, quick-setting epoxy or spot welding prior to or during initial installation. Once the transducer assembly is clamped to the conduit, the coupler remains fixed in position by the clamping force. Suitable tabs may extend at the front and back, or at the sides, of the transducer assembly.

FIG. 2A is a cut-away view, somewhat enlarged in scale, of the coupler clamped in position between the conduit wall 20 and ultrasonic signal assembly 6. As shown, the conduit wall has a surface 22 which may include roughness such as fairly regular undulations extending along a circumferential band due to turning marks, or transverse ridges due to machine chatter or other machine marks, or irregular bumps or casting roughness in a stippled or irregular pattern. As shown, the coupling device 30 conforms to the pipe surface and contour without appreciably spreading or losing its mechanical integrity. Furthermore the barrier layer 31 is sufficiently thin to contact and conform to the outer wall 22 of the conduit so that good acoustic contact is made by the combined compliance due to the thinness in layer 31 and low modulus of the layer 32. In theory it might seem that the sandwich couples only along a line or at a point where the end of the presumably-flat waveguide is tangent to the cylindrical or spherical tank or conduit. In practice, where the radius of curvature of the tank or conduit exceeds about one inch, the resilient sandwich coupler having a total thickness about 150 micrometers (six mils) flows to fill the gap.

Figure 3:
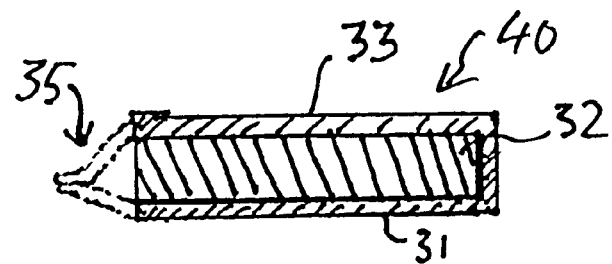
FIG. 3 illustrates a second embodiment of the invention as viewed in cross-section.

FIG. 3 illustrates a second embodiment 40 of a coupling device in accordance with the present invention, with corresponding layers numbered identically to those of device 30 in FIGS. 1–2A. As shown, a first barrier layer 31 is covered by a second compliant layer 32, which in turn is covered by a further barrier layer 33. In the illustrated embodiment, barrier layer 33 is simply a continuation of layer 31, and it may be formed, for example, in a gold foil embodiment by folding over the foil layer 31 to cover the coupling layer 32, thus forming a closed sandwich with barrier layers at the top and bottom. As shown, the foil may also be extended around the other edge of layer 32, so that top and bottom layers are joined together at 35 forming a complete envelope about the middle layer and enclosing it against the surrounding environment. In this embodiment, i.e., with layers 31 and 33 above and below layer 32, the coupling element 40 is symmetric top to bottom so that no matter how a user installs it, i.e., "right side up" or upside-down ', a barrier layer 31 or 33 lies in contact with the conduit wall 22. Thus, when the coupling layer 32 is a relatively reactive, mobile or low melting point material such as zinc that might diffuse into, or alloy at high temperature with, the material of the conduit wall and undesirably change its physical properties, the barrier layers assure that good coupling is achieved without introducing a risk of physical or chemical deterioration of the conduit itself. Further, when layer 32 is entirely enveloped by being totally surrounded with barrier material, the coupling sheet 32 is itself better protected from reactive fumes such as often exist in plant environments where clamp-on coupling to hot pipe is required.

In some embodiments either the barrier or second layer can be plated. Zinc, however, can not easily be coated with gold. Furthermore, plating to thicknesses of one or two mils is time-consuming and expensive, and may produce a coating that is too hard. Electroformed nickel can be built up to two mils, but the desired coupling properties are not necessarily achieved with that process. Hence, in most cases, fabrication of the coupler with separate foil layers is preferred.

It will be appreciated that the thicknesses of the various layers 31, 32 (and 33 if present) may vary in other embodiments to accommodate different conduit surface roughness, curvature or temperature conditions, and the materials thereof may also vary. By way of example, commercial embodiments of the hockey stick buffer shown in U.S. Pat. No. 6,047,602 have a width of about a quarter inch, so that when clamped tangent in an axial plane to a two inch OD conduit, the drop off or gap increase due to conduit curvature is about 2.5 mils, at the sides of the contact face the 5–6 mil layered constructions of the above-described couplers are sufficient to "fill the gap" between conduit and coupler uniformly. For other signal buffer assemblies, such as a 1-inch diameter flat buffer as described in U.S. Pat. No. 5,952,790, when coupling to a spherical surface, the coupler itself may vary in thickness, being plano-concave or plano-convex to more readily fill the gap. For shaped or thicker couplers, the material may also be chosen with a sound speed effective to reduce any potentially undesirable lensing action.

In general the barrier layer is to be thin, inert or non-reactive, and relatively strong and not permeable. Examples of satisfactory barrier materials are gold, platinum or nickel, pre-annealed or annealed by exposure to the hot conduit or wall. The second layer may have a lower modulus, and be more reactive. Metals such as zinc, lead, tin, soft copper and the like, are considered suitable to the extent compatible with prevailing temperature and environment at the intended installation, including health and safety issues. In some cases a high-temperature plastic material could serve as the coupler. Examples include DuPont's Vespel, and Celanese-Hoecht's Celazol. Plastic, if used in the sandwich, must be capable of long-term coupling without creeping or shearing. Preferably the coupler should also have an acoustic impedance Z and sound speed c close to that of the waveguide or wall, so metals will generally come closer to the desired set of properties, than a plastic.

For cryogenic applications, and taking into account the fact that "cryogenic" pipes often remain for extended periods at ordinary temperatures, which in outdoor sunlight may rise to over 40° C., the second layer may even be formed of a material such as indium, with the barrier layer then serving as a barrier against alloying with the pipe wall or reacting with environmental gases. The couplers of the present invention may be provided as die-cut individual layers, or as pre-assembled pads or thin stacks of the described foils or sheets, which may further, for example have a suitable thin contact adhesive securing the different lamina together at their outer edges, and/or disposed on an outer face thereof to facilitate installation. These are preferably compounded or applied such that no residue remains that would interfere with coupling. The stacks, pads or sheets may be shaped to fit the contact area of the intended transducer, wedge or mounting block.

The invention being thus disclosed and illustrative embodiments depicted herein, further variations and modifications of the invention, will occur to those skilled in the art, and all such variations and modifications are considered to be within the scope of the invention, as defined by the claims appended hereto and equivalents thereof.

What is claimed is:

1. An article for coupling an ultrasonic signal to a hot wall, such article comprising
    a barrier layer configured for directly contacting the wall and
    a supplementary layer of coupling material extending over the barrier layer and being effective to provide acoustic signal coupling without deterioration of the wall when clamped with said barrier layer between an ultrasonic signal assembly and the wall.

2. The article of claim 1, wherein said barrier layer is an inert metal foil and said supplementary layer comprises a low-modulus metal sheet.

3. The article of claim 2, further comprising a cover layer of said inert material, wherein said barrier layer and said cover layer enclose the supplementary layer.

4. The article of claim 3, wherein said article has a size and shape conforming to the contact area of an ultrasonic signal device.

5. The article of claim 4, wherein the article includes a mounting tab for mounting to said ultrasonic signal device.

6. The article of claim 1, formed as an open sandwich.

7. The article of claim 3, formed as a closed sandwich.

8. The article of claim 1 where the thickness of the barrier layer exceeds conduit surface roughness by a factor of at least two.

9. A method of coupling an ultrasonic signal element to a wall surface, such method comprising the steps of
    providing a layer of barrier material against the wall surface
    providing a sheet of acoustic coupling material over the layer of barrier material, and
    clamping the layer of barrier material and the sheet of coupling material between the ultrasonic signal element and the surface to effect ultrasonic coupling, wherein the step of providing said layer of barrier material includes providing a foil layer of inert metal as a barrier against migration or alloying of material from said sheet of coupling material.

10. The method of claim 8, wherein the step of providing said layer of barrier material includes providing a foil layer selected from among a gold foil, a platinum foil and a nickel foil.

11. The method of claim 8, wherein the sheet of acoustic coupling material has a thickness and modulus effective to couple an ultrasonic signal through surface roughness into the wall.

12. The method of claim 8, wherein the sheet of acoustic coupling material has a thickness greater than approximately one hundred micrometers.

13. The method of claim 8, wherein the sheet of coupling material has a thickness effective for coupling a planar surface of the ultrasonic signal element to a curved contour of a conduit surface.

14. The method of claim 8 where said coupling material is selected from among tin, zinc, indium or silver, or their alloys having melting or eutectic point at least 20° C. above an intended application temperature.

15. A method of coupling an ultrasonic signal element to a solid wall, such method comprising the step of
    clamping a multi-layered sandwich structure including a barrier foil and a compliant sheet between the ultrasonic signal element and the solid wall
    wherein the foil contacts the wall forming a barrier to the compliant sheet.

16. The method of claim 15, wherein the foil encloses the compliant sheet.

17. The method of claim 15, wherein the compliant sheet has a thickness effective to comply with a surface of said wall.

18. The method of claim 15, wherein the foil has a thickness effective to comply with surface roughness of said wall.

* * * * *